United States Patent [19]
Berndt et al.

[11] Patent Number: 5,432,061
[45] Date of Patent: Jul. 11, 1995

[54] METHOD AND APPARATUS FOR DETECTING MICROORGANISMS

[75] Inventors: Klaus W. Berndt, Stewartstown, Pa.; Thomas H. Schulte, Glen Arm, Md.

[73] Assignee: Becton Dickinson and Company, Franklin Lakes, N.J.

[21] Appl. No.: 938,968

[22] Filed: Sep. 1, 1992

[51] Int. Cl.⁶ .............. C12Q 1/04; C12M 1/34; G01N 21/00
[52] U.S. Cl. .................. 435/34; 435/291; 435/296; 435/808; 356/39; 356/318; 356/417
[58] Field of Search ............ 435/3, 29, 34, 39, 32, 435/287, 289, 291, 296, 808; 422/82.07, 82.08, 82.06; 364/413.1; 250/461.2, 461.1; 356/39, 73, 338, 339, 317, 318, 417

[56] References Cited

U.S. PATENT DOCUMENTS

| | | | |
|---|---|---|---|
| 3,916,197 | 10/1975 | Fulwyler | 250/361 |
| 3,926,738 | 12/1975 | Wilson et al. | 435/289 |
| 4,152,213 | 5/1979 | Ahnell | 435/39 |
| 4,314,029 | 2/1982 | Ohtake et al. | 435/291 |
| 4,889,992 | 12/1989 | Hoberman | 435/39 |
| 4,940,332 | 7/1990 | Miwa et al. | 356/417 |
| 4,945,060 | 7/1990 | Turner et al. | 435/291 |
| 4,952,498 | 8/1990 | Waters | 435/34 |
| 4,971,900 | 11/1990 | Ahnell et al. | 435/29 |
| 5,155,019 | 10/1992 | Sussman et al. | 435/291 |
| 5,217,875 | 6/1993 | Karpf et al. | 435/291 |
| 5,232,839 | 8/1983 | Eden et al. | 435/34 |

FOREIGN PATENT DOCUMENTS

| | | |
|---|---|---|
| 0061809 | 10/1982 | European Pat. Off. . |
| 0264221 | 4/1988 | European Pat. Off. . |
| 0301600 | 2/1989 | European Pat. Off. . |
| 4016260A1 | 12/1990 | Germany . |
| 2102947 | 2/1983 | United Kingdom . |
| WO90/13663 | 11/1990 | WIPO . |

OTHER PUBLICATIONS

Lakowicz et al., "Photon Migration in Scattering Media and Tissue", Proceedings SPIE, pp. 468–479, 1990.
"Bact/Alert: an Automated Colorimetric Microbial Detection System", Journal of Clinical Microbiology, Jul. 1990, pp. 1608–1615 (Thorpe et al.).

Primary Examiner—Robert J. Warden
Assistant Examiner—Theresa T. Snider
Attorney, Agent, or Firm—Alan W. Fiedler

[57] ABSTRACT

The present invention describes a method and apparatus for detecting microorganisms in a large number of blood culture vials using more than one microorganism detection principle for each vial. Two of such possible detection means includes the use of a fluorescent carbon dioxide sensor and scattered photon migration. The apparatus performs a logic linkage of the results of all the detection principles applied. Therefore, an enhanced recovery and an improved accuracy in detecting microorganisms is achieved.

21 Claims, 8 Drawing Sheets

METHOD AND APPARATUS FOR DETECTING MICROORGANISMS

BACKGROUND OF THE INVENTION

The present invention relates to methods and apparatus for detecting microorganisms in blood culture samples, where the specimen and a culture medium are introduced into a sealable container or vial and are exposed to conditions enabling a variety of metabolic, physical, and chemical changes to take place in the presence of microorganisms within a sample.

Usually, presence of biologically active agents such as bacteria in a patient's body fluid, especially blood, is determined using blood culture vials. A small quantity of blood is injected through the enclosing rubber septum into the sterile vial containing a culture medium. The vial is incubated at 37° C. and monitored for bacterial growth.

Common visual inspection involves monitoring the turbidity or eventual color changes of the liquid suspension. Known instrumental methods detect changes in the carbon dioxide content of the culture bottles, which is a metabolic by-product of the bacterial growth. Monitoring the carbon dioxide content can be accomplished by methods well established in the art, such as radiochemical, or infrared absorption at a carbon dioxide spectral line. These methods require invasive procedures which result in the well-known problem of cross-contamination between different vials. For purposes of this application, the term invasive implies that the confines of the vial must be entered in order to determine if microorganisms are present, e.g., a probe is inserted into a sealed vial. In addition, due to the fact that head space gas (i.e. the gas in the vial above the sample) must be removed for analysis, there is a requirement for adding head space gas to the vials after each measurement.

It has also been proposed to detect bacterial growth in sealable containers by monitoring positive and/or negative pressure changes (e.g., U.S. Pat. No. 4,152,213—Ahnell, the disclosure of which is incorporated by reference). Any temperature change within the vial head space, however, generates a pressure change which is not related to biological activities. Therefore, a head space temperature measurement is required in order to distinguish between biological and temperature-generated pressure changes. Non-invasive head space temperature monitoring, however, is a difficult problem. Additionally, some microorganisms can produce high pressure values, while others produce relatively low or negligible changes. Thus, any pressure sensor used must be sensitive enough to allow detection of small changes in pressure while also being capable of safely measuring high pressure values. These two requirements are often mutually exclusive depending on the type of pressure sensor technology used. As a result, some microorganisms may be difficult to detect by pressure monitoring using available technology.

Recently, non-invasive methods have been developed involving chemical sensors disposed inside the vial. These sensors respond to changes in the carbon dioxide concentration by changing their color or by changing their fluorescence intensity. (See, e.g. Thorpe et al. "BacT/Alert: An Automated Colorimetric Microbial Detection System", *J. Clin. Microbiol.*, July 1990, pp. 1608-12, and U.S. Pat. No. 4,945,060—Turner, et al., the disclosure of which is incorporated by reference). These techniques are based on light intensity measurements and require spectral filtering in the excitation and/or emission channels. With these techniques, errors can occur if the light source, the photodetector, the filters, or the sensor show aging effects over time which would vary the intensity response. Additionally, certain species of microorganisms are weak carbon dioxide producers. Therefore, it is possible that sensors based on carbon dioxide monitoring may fail to detect certain microorganisms.

It has been suggested in U.S. patent application Ser. No. 07/874,324, the disclosure of which is incorporated by reference, to take advantage of changes in the hemoglobin absorption as well as changes in light scattering caused by bacterial activities in blood cultures. This detection principle is based on scattered photon migration (SPM) in a highly absorbing and highly scattering medium whereby, no diffusion effect into a sensing membrane takes place, and no corresponding delay time is observed. However, if the SPM detection method is used alone, one loses the benefit of the carbon dioxide detection method, which is able to detect most of the microorganism species.

SUMMARY OF THE INVENTION

The present invention describes a method and apparatus for detecting microorganisms in samples, most preferably a culture medium and blood specimen placed in a container such as a sealed vial, using for the first time in combination more than one microorganism detection principle for each vial. The instrument performs a logic linkage of the partial answers of all detection principles applied. Therefore, an enhanced detection and an improved accuracy in detecting microorganisms is achieved. An apparatus according to the present invention can perform multiple tests on a minimum number of vials, and can therefore save labor time and cost. An additional beenfit to the patient is that less blood has to be drawn.

It is an objective of the present invention to overcome the above described problems of the prior art by providing a method and apparatus for detecting microorganisms in blood culture vials that exhibits a significantly reduced probability of detection failure, and that therefore allows for an enhanced recovery and improved accuracy in detecting microorganisms.

According to the present invention, the above objective is achieved through a multi-step process. First, a culture medium and blood specimen are introduced into one or more sealable vials. Second, each vial is monitored for microorganism growth with more than one detecting means, based on more than one physical, chemical, or metabolic parameter. Third, these partial system answers are linked by the development of dedicated correlating algorithms to generate a final system determination of the presence or absence of bacteria.

A first preferred embodiment of an apparatus according to the present invention comprises a number of sealed blood culture vials containing the culture medium and the blood specimen. All vials are arranged within an incubator which maintains a temperature which provides for optimum growth conditions, such as 37° C. The apparatus includes at least two different detecting means that are utilized to interrogate each vial for bacterial growth. The two or more detecting means can be arranged adjacent to each vial, or can be moved to each vial to interrogate the vials serially. It is also possible to move the vials serially to the detecting means. For certain detection principles the detecting means can be located partially within the vials, e.g. in the case of fluorescent or colorimetric sensors. The sensing means, however, can also be located completely outside the vials, e.g. in the case of scattered photon migration (SPM).

The detecting means are connected to a system controller such as a computer. The controller activates the detecting means and receives the detection data, which may be stored within the controller. Finally, the controller may be connected to a peripheral modem which allows the initiation of the measurement process as well as the collection of information regarding the detection of microorganisms.

In operation, the controller activates the different detecting means and receives and stores the data. The data is then typically analyzed within the controller. This analysis is performed separately for each detecting means, based on proven detection algorithms. For each detecting means, a partial system answer is generated. It is also possible to perform a cross-correlation procedure between two or more output signals obtained from the detection means. Finally, the computer generates an overall system answer, and transmits this to the peripheral modem.

The system recovery is even more enhanced, the accuracy is improved further, and the instrument self-testing capability is increased substantially if more than two sensor or detection principles are combined within one instrument. It is significant that the cost per sensor principle decreases when more than one such principle is used. This is because such system components as the incubator, light sources or detectors, and the system controller can be utilized for more than one detecting means. Therefore, the performance versus cost ratio of an apparatus according to the present invention is better than in other known systems.

BRIEF DESCRIPTION OF THE DRAWINGS

The various features, objects, benefits, and advantages of the present invention will become more apparent upon reading the following detailed description of the preferred embodiments along with the appended claims in conjunction with the drawings, wherein reference numerals identify corresponding components, and:

DETAILED DESCRIPTION OF THE PREFERRED EMBODIMENTS

Figure 1:
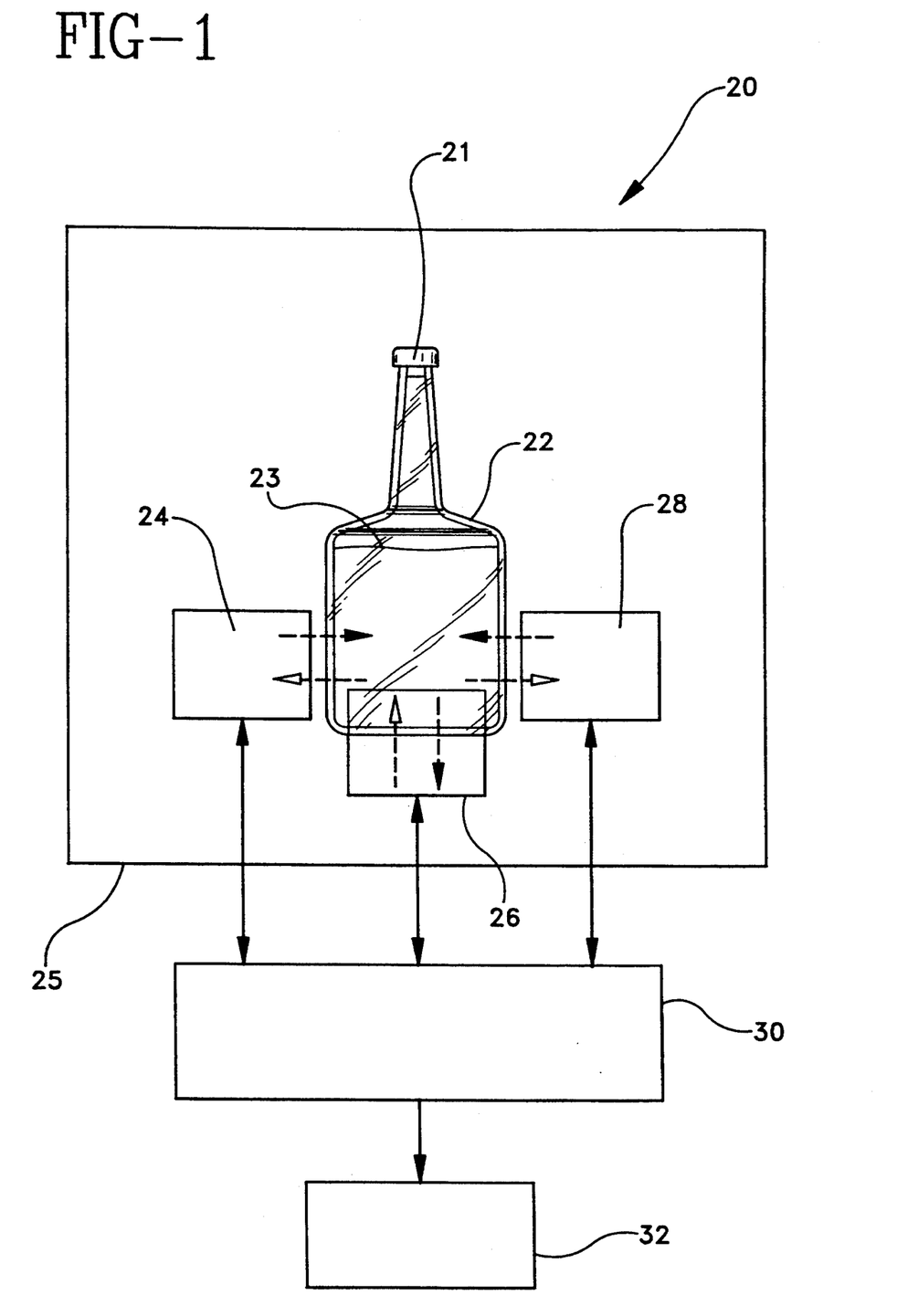
FIG. 1 illustrates schematically an apparatus for detecting microorganisms in blood culture vials according to the present invention.

One embodiment of a detection apparatus 20 embodying the principles and concepts of this invention is depicted schematically in FIG. 1. The disclosed apparatus comprises glass vials 22 sealed with a septum 21 and containing a medium/blood mixture 23. All vials are arranged within an incubator 25 which maintains a temperature of 37° C. in order to allow for optimum growth conditions. The apparatus also comprises three different detection means 24, 26, and 28 that are utilized to interrogate each vial for bacterial growth. The detecting means 24, 26, and 28 are arranged adjacent to each vial 22. In the preferred embodiment, a portion of detecting means 26 is located partially within the vial. Detecting means 26 could, for example, include a fluorescent sensor. Detecting means 24 and 28 are located completely outside vial 22.

The detecting means 24, 26, and 28 are connected to a system controller 30, which may be a computer. System controller 30 activates the detecting means 24, 26, and 28 and receives data from them, which is stored within the system controller. In this embodiment, system controller 30 is also connected to a peripheral modem 32 which allows an operator to initiate the measurement process, and to obtain information regarding the detection of microorganisms.

In operation, the system controller 30 activates the different sensing means 24, 26, and 28 and receives and stores the data. The data is then analyzed within system controller 30. This analysis can be performed separately for each detecting means 24, 26, and 28, based on proven detection algorithms for each detecting means. Then, for each detecting means, a partial system answer is generated.

There are three possible partial answers for each sensing means. First, the application of the detection algorithm can yield the partial answer "detection positive". Second, the detection algorithm can yield the answer "detection negative". Third, the partial answer can be "decision impossible". This last partial answer can happen if, for example, the received signal level is too low, or if the noise contributions to the signal are too high.

As a matter of experience with regard to all known detection principles, sometimes the partial answers 1 and 2 can be wrong. These detection failures are known as "false-positive" and "false-negative", respectively. This has been observed when parallel detection experiments are performed on different automated blood culture instruments.

If there is only one detection principle available, there is insufficient information to determine if the decision is right or wrong.

A common way to improve the detection accuracy is to place more than one vial with the same specimen into the instrument. However, this additional measure requires more blood, more space within the instrument, and more labor time. The present invention overcomes these disadvantages to a high degree.

To those skilled in the art, there are many possible ways to link or correlate the data of different detecting means that are arranged within one instrument. As discussed above, each detecting means can produce its own partial answer. The different answers can then be correlated by applying known principles of logic. It is, however, also possible to link together the data itself by applying known principles of correlation theory. If, for instance, the output signals of two or more detecting means exhibit a low signal-to-noise ratio, then the application of kinetic detection algorithms to the individual signals becomes almost impossible. If, however, these signals are cross-correlated, noise contributions can be averaged out to a high degree and only growth-related signal changes will remain in the output signal. In other words, an apparatus according to the present invention offers an opportunity to shorten the time necessary to detect bacterial growth. Finally, system controller 30 generates an overall system answer, and transmits this to the peripheral modem 32.

Figure 2:
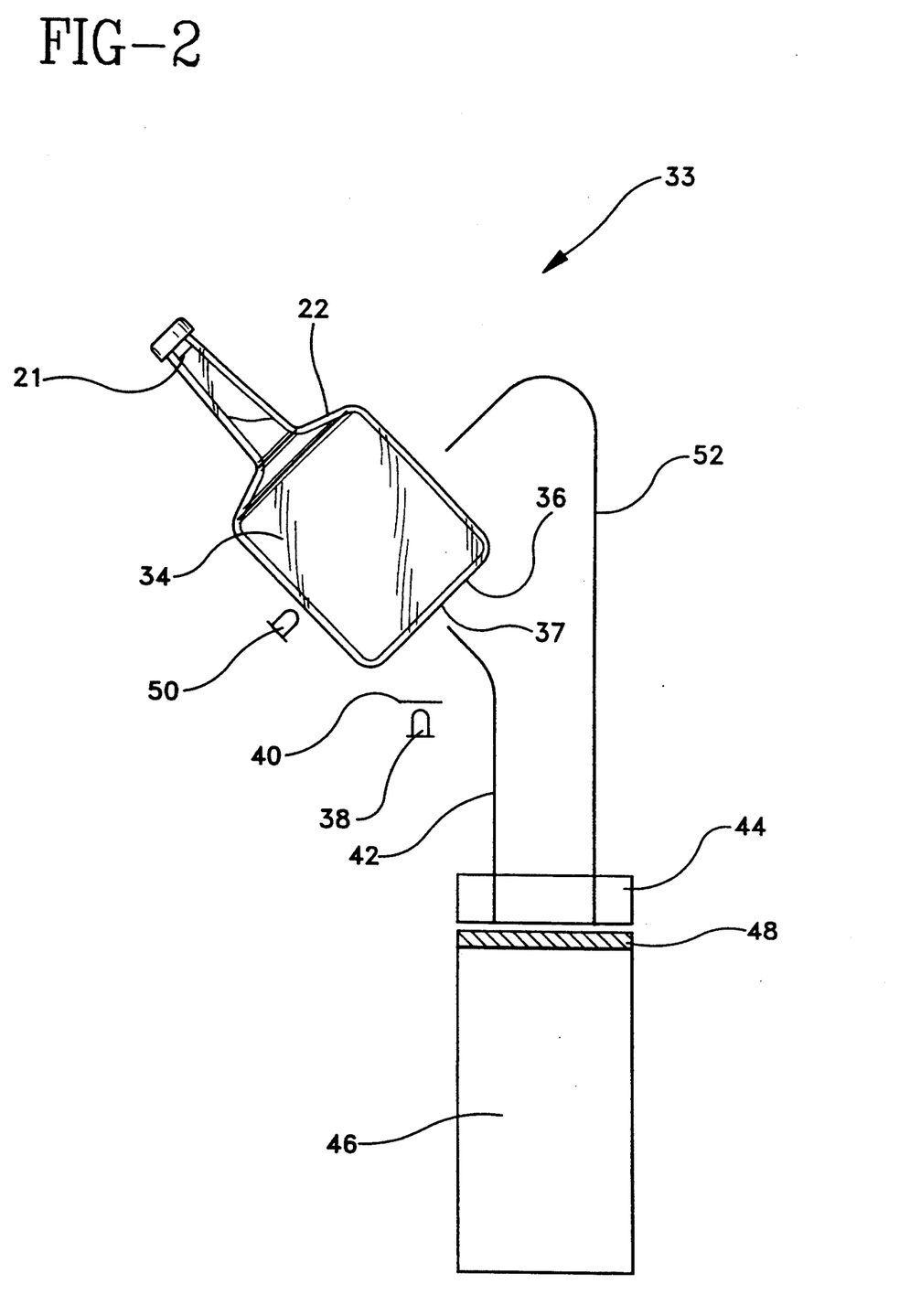
FIG. 2 shows as an example the combination of a fluorescent sensor and detecting means based on scattered photon migration.
Figure 3A:
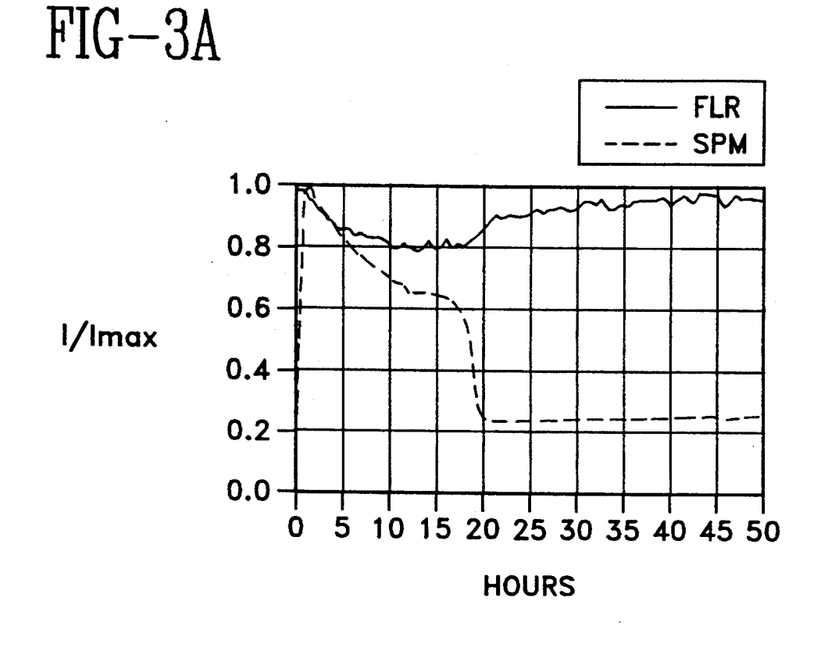
FIGS. 3A to 3D show original plots obtained on an apparatus according to the present invention, with a fluorescent carbon dioxide sensor (solid lines) and detecting means based on scattered photon migration (dashed lines).
Figure 3B:
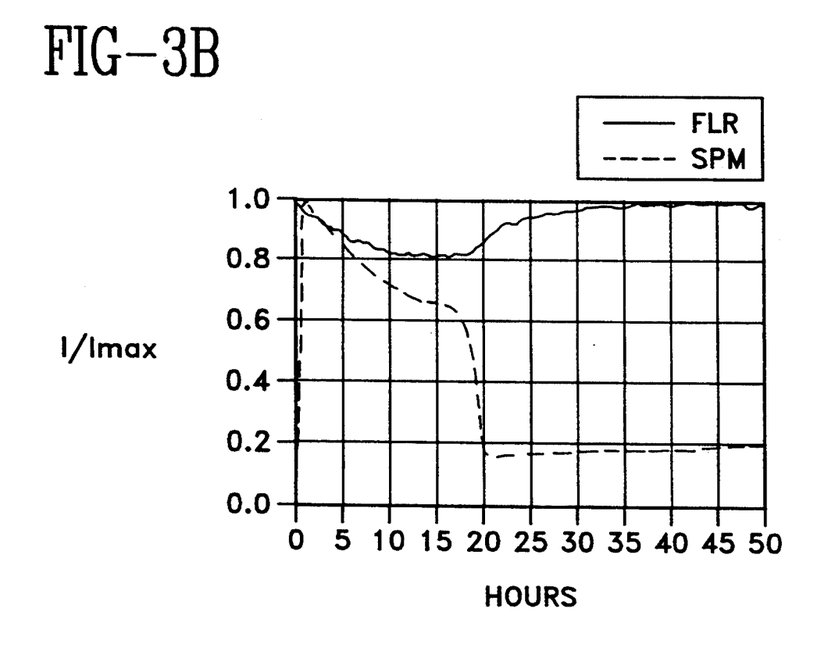
Figure 3C:
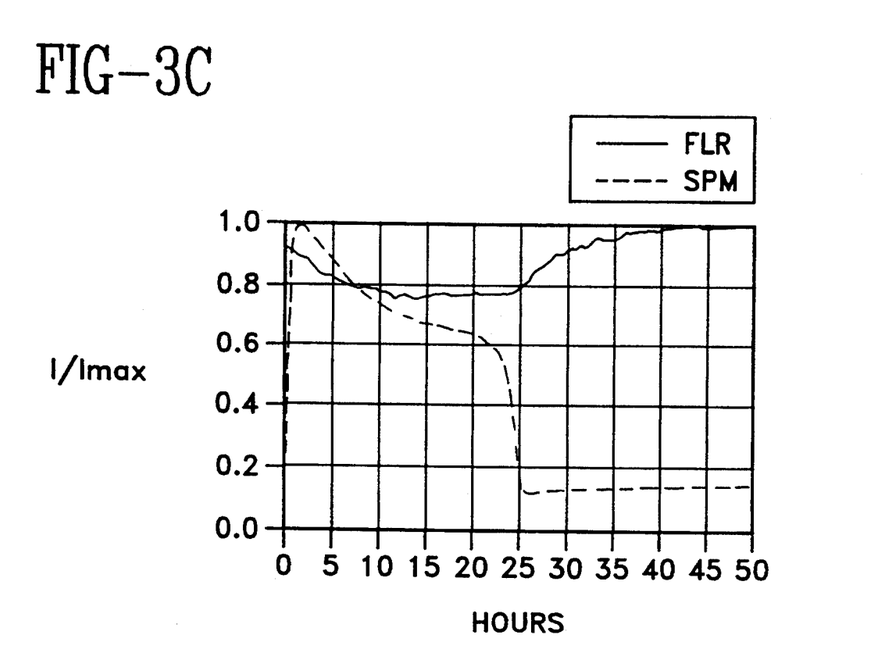
Figure 3D:
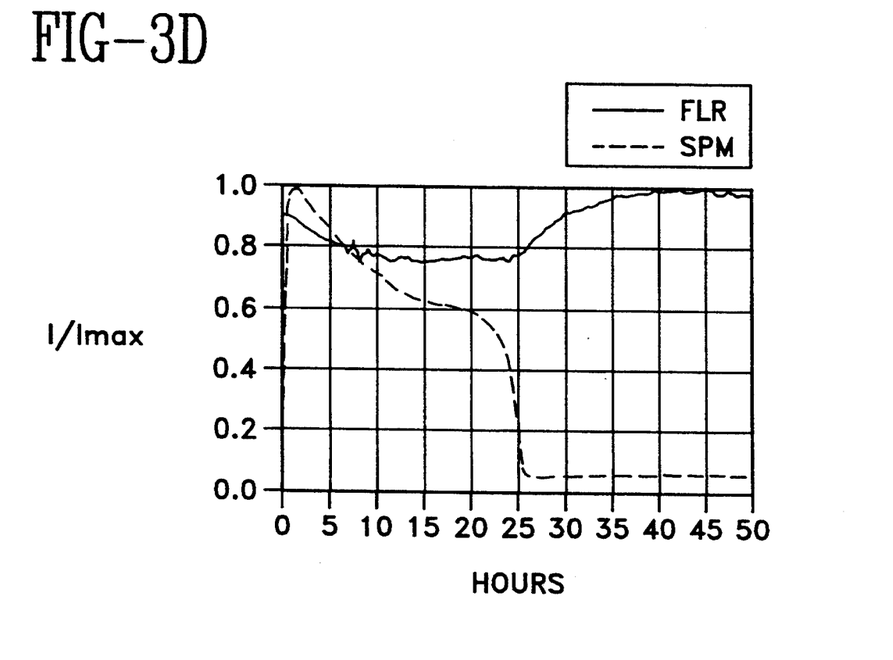
Figure 4A:
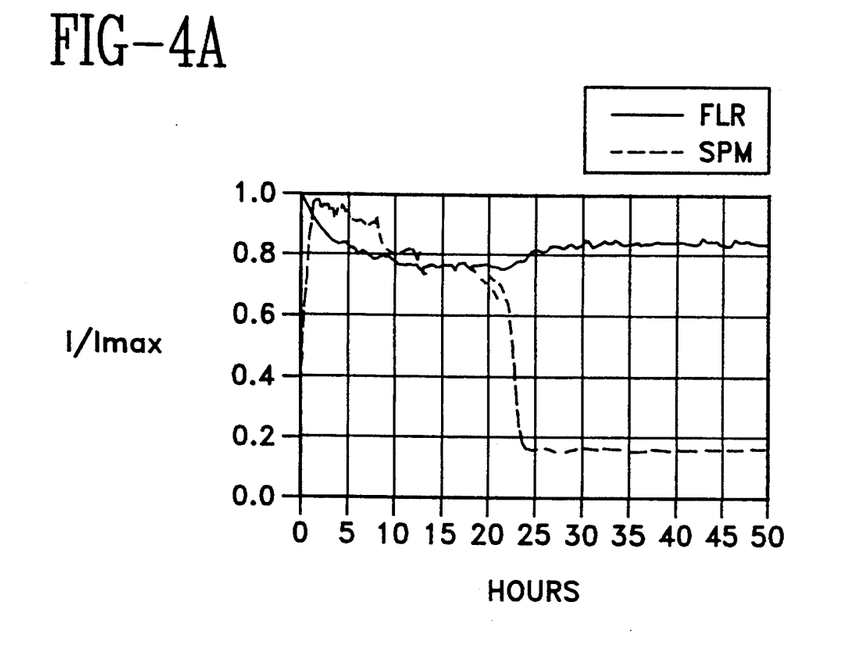
FIGS. 4A to 4D show original plots obtained on an apparatus according to the present invention, with a fluorescent carbon dioxide sensor (solid lines) and detecting means based on scattered photon migration (dashed lines).
Figure 4B:
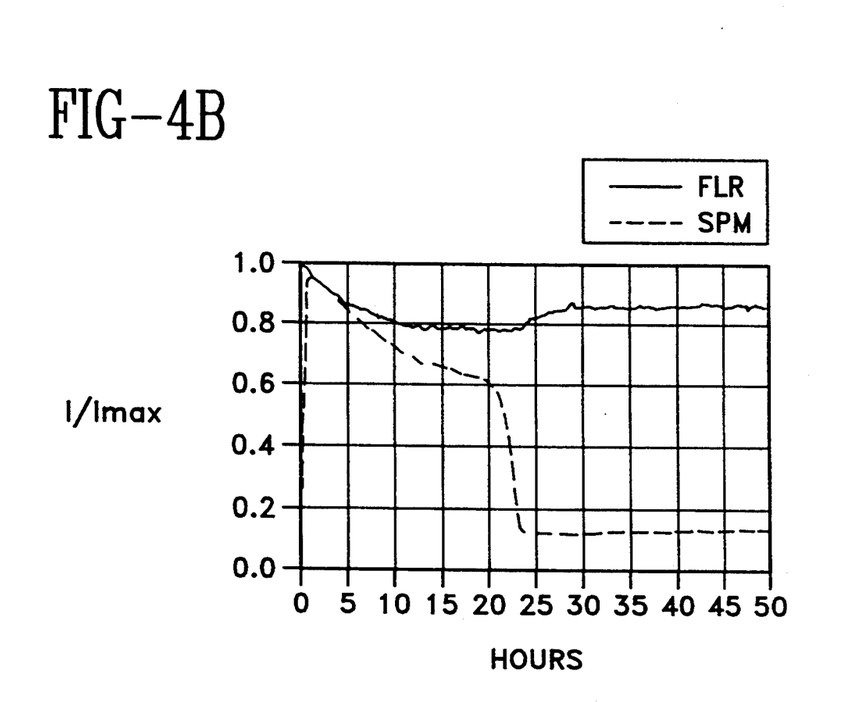
Figure 4C:
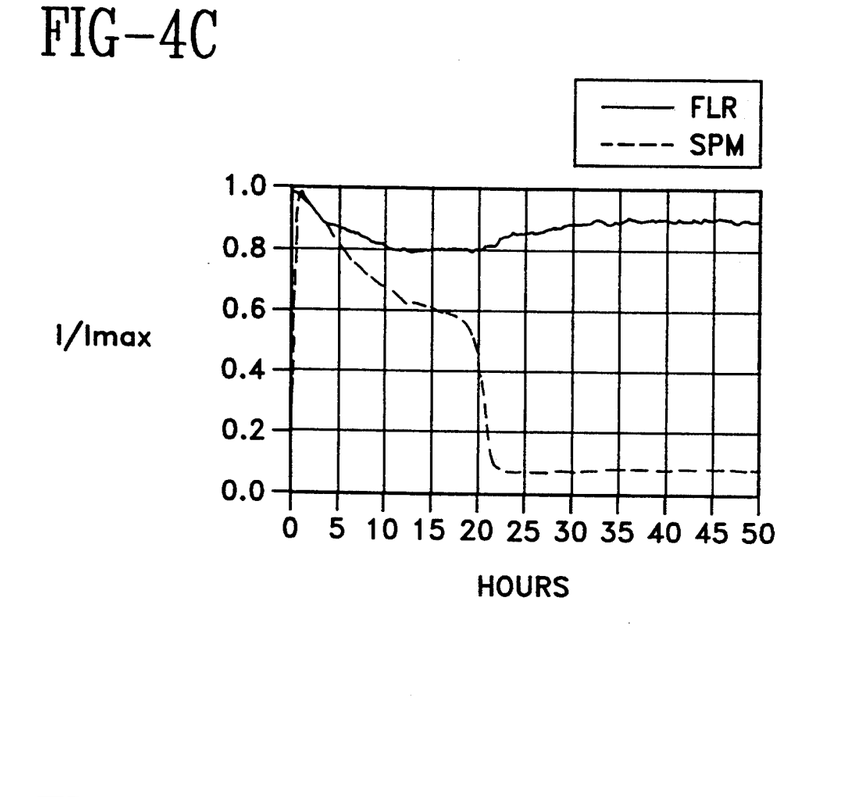
Figure 4D:
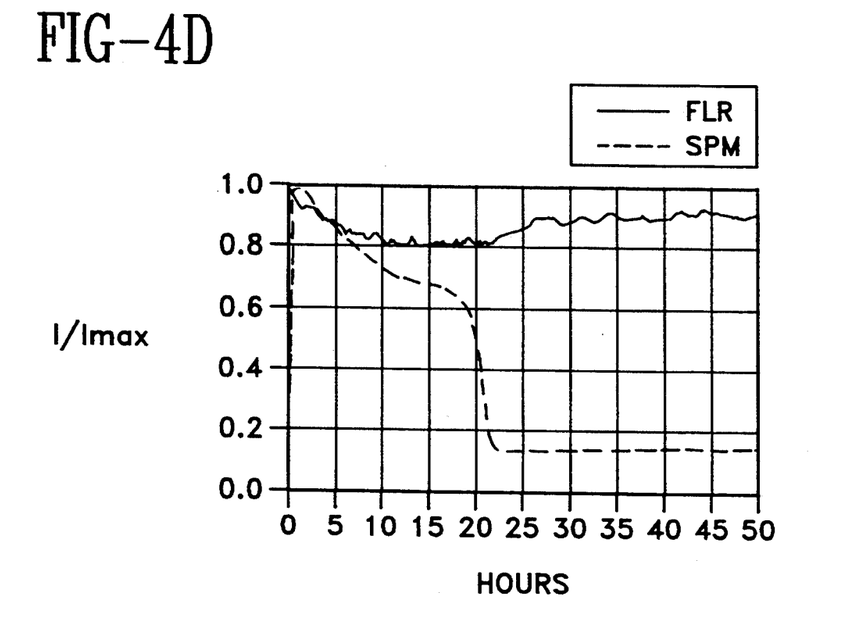
Figure 5A:
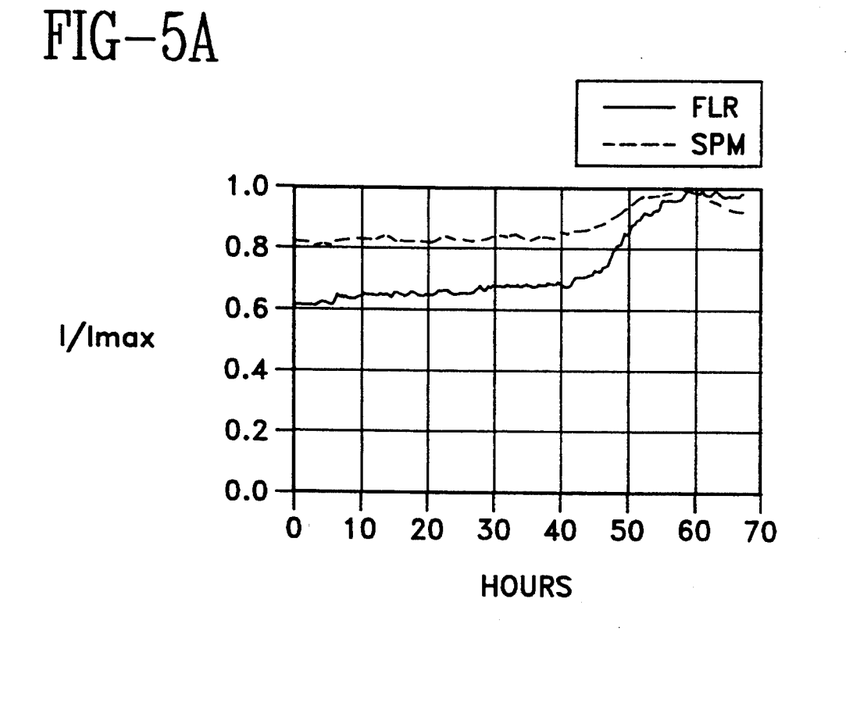
FIGS. 5A to 5D show original plots obtained on an apparatus according to the present invention, with a fluorescent carbon dioxide sensor (solid lines) and detecting means based on scattered photon migration (dashed lines).
Figure 5B:
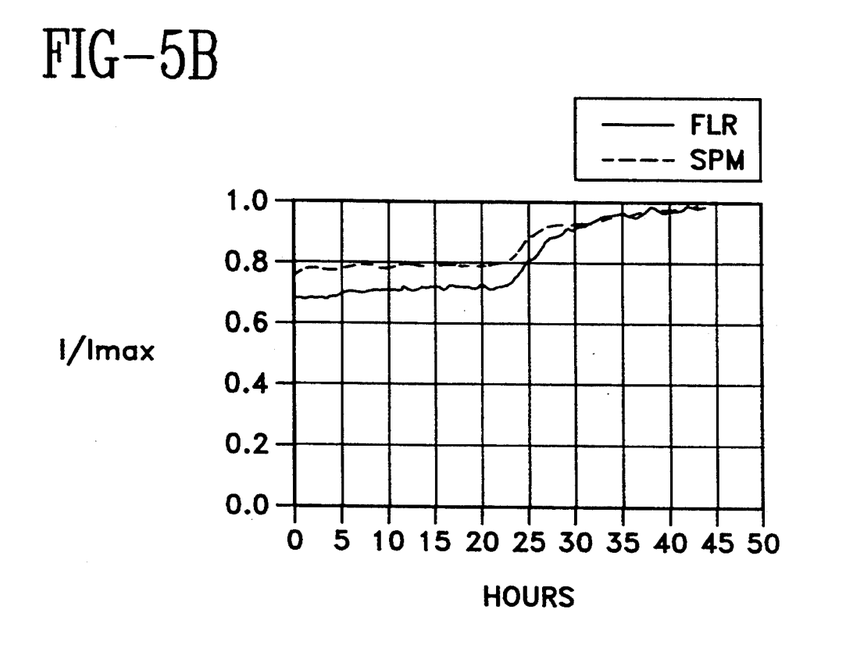
Figure 5C:
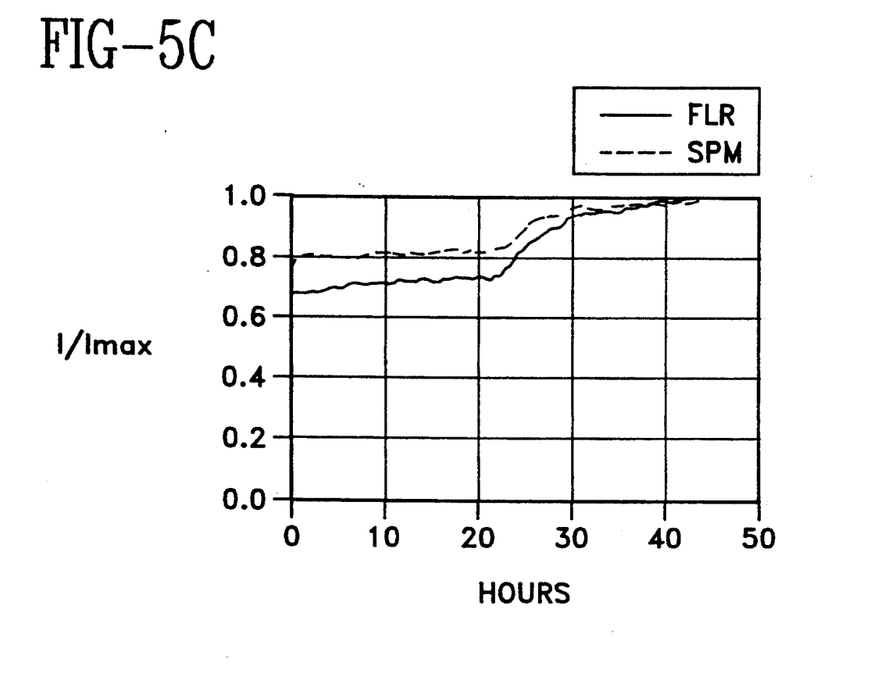
Figure 5D:
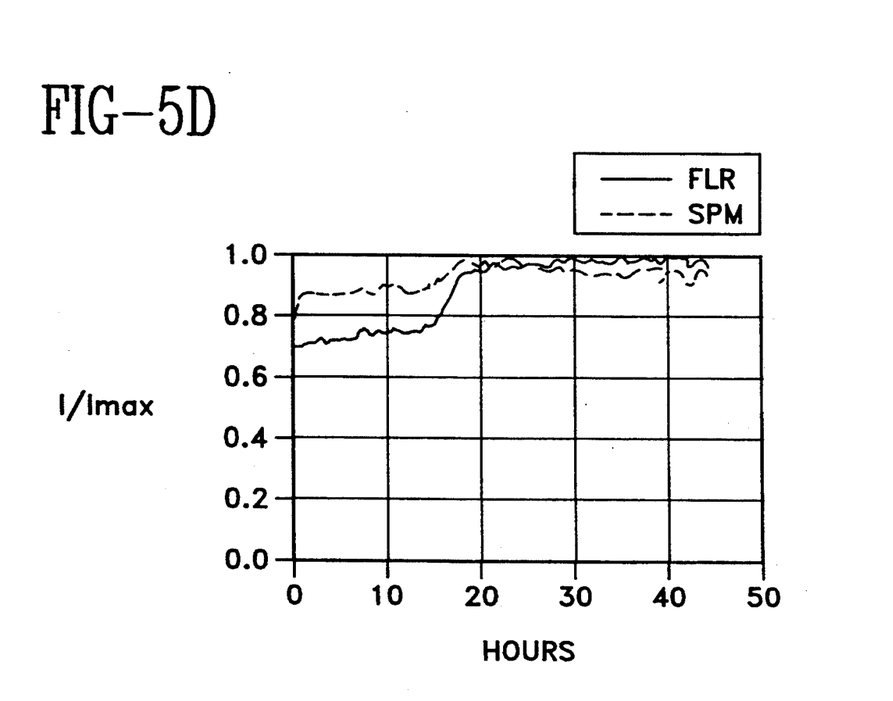

FIG. 2 shows, as one preferred embodiment, the combination of a fluorescent sensor and detecting means based on scattered photon migration (SPM) within one instrument. The apparatus 33 includes a number of glass vials 22, sealed with a septum 21 and containing a medium/blood mixture 34. All vials 22 are arranged within an incubator which maintains a temperature of 37° C. in order to allow for optimum growth conditions.

Each vial 22 contains a fluorescent carbon dioxide sensor 36 spread to the inner vial bottom 37. The sensor 36 is excited by means of a green light emitting diode 38. A green emitting diode is preferred because of the short-wavelength light it produces which reacts favorably with sensor 36. A spectral filter 40 is arranged between the light emitting diode 38 and the sensor 36 to block unwanted long-wavelength radiation which can affect readings. In practice, the fluorescence intensity of sensor 36 increases as the carbon dioxide concentration present in a vial 22 increases. Thus, more of the light from diode 38 is emitted by sensor 36 as microorganisms grow. Fluorescence light emitted by the sensor is collected by one end of an optical fiber 42. The other end of all such fibers 42 are mounted within an opaque plate 44. Fluorescence light reemerging from the fibers 42 at the plate 44 is detected by a high-sensitivity photodetector 46 such as a photomultiplier. Typically, a photomultiplier converts the light received into an electrical signal that is proportional to intensity. A spectral filter 48 is arranged in front of photodetector 46 to prevent scattered green excitation light from reaching the photodetector 46, and adversely affecting the readings.

The second detecting means utilized in apparatus 33 is based on scattered photon migration. Biological activities (e.g., microorganism growth) within a culture medium, such as a blood culture medium, will result in a change in the reemerging intensity of light introduced into the medium. Therefore, biological activities such as bacterial growth can be detected by monitoring the reemerging light intensity. In the disclosed embodiment, the second detecting means comprises a red light emitting diode 50 adjacent to each vial 22. Part of the red light reemerging from the medium 34 is collected by a second optical fiber 52. An end of all such fibers 52 terminate in plate 44 in front of the photodetector 46. For this particular embodiment, only one red light emitting diode 50 and only one additional optical fiber 52 are required to upgrade the blood culture system from a single principle instrument to a two-principle instrument. Thus, a much more accurate device may be constructed at a greatly reduced additional cost.

The partial answers are generated as discussed above. When two detection principles are applied, as in this embodiment, the possible decisions can be distributed as shown in the following table.

TABLE 1

Possible decision distribution for two sensor principles.

| CASE | 1 | 2 | 3 | 4 | 5 | 6 | 7 | 8 | 9 |
|---|---|---|---|---|---|---|---|---|---|
| PRINCIPLE #1 | + | − | + | − | + | − | 0 | 0 | 0 |
| PRINCIPLE #2 | + | − | − | + | 0 | 0 | + | − | 0 |

In Table 1, the + sign stands for "detection positive", the − sign stands for "detection negative" and a 0 indicates "decision impossible".

The apparatus 33 shown in FIG. 2 provides significantly more information as compared to a single detection principle device. If for instance both detection principles yield the partial answer "detection positive" (case 1), and if both principles are based on different microbiological effects, then the likelihood for a detection failure is substantially lower. The same considerations apply if both principles yield the partial answer "detection negative" (case 2). Additionally, there is a much greater likelihood that the right overall answer is being generated. If, however, the two principles yield conflicting partial answers (cases 3 and 4), then the detecting means are producing clear signals but one of them does not recover a growing microorganism.

In general, different detection principles have their specific weaknesses. For instance, the fluorescent carbon dioxide-based sensor 36 will perform imperfectly with microorganisms that are low carbon dioxide producers. In this case, the detecting means based on scattered photon migration, which responds to changes in hemoglobin oxygenation and/or light scattering, will perform much better. On the other hand, if the SPM detection method is used alone, one loses the benefit of the carbon dioxide detection method, which is able to detect most of the microorganism species. Therefore, combining at least two sensor principles within one automated blood culture system should broaden the recovery range compared to a one-principle system. In cases 3 and 4 of Table 1, the information suggests that the presence of a growing microorganism is likely, but a repeat experiment based on an alternative detection principle is recommended.

Cases 5 to 8 in Table 1 reflect a different system status. In cases 5 and 6, the output states that detecting means #2 may have a technical problem. Yet, the partial answer from detecting means #1 may still be taken into consideration. The same amount of information is being received as would be obtainable from a one-principle blood culture system. In addition, information is provided which suggests that either the particular sample shows unusual characteristics, or the detecting means #2 is defective and requires service. An equivalent situation is reflected by cases 7 and 8. Here, the detecting means #1 may require service.

Case 9 indicates that there exists a high probability for a technical instrument failure, and that immediate service is indicated. It should be noted, however, that in an automated blood culture systems with detecting means at each vial, all other stations may still work perfectly even though a single vial station may have a technical instrument failure. Thus, an apparatus according to the present invention offers the additional advantage of an improved instrument self-testing capability.

In an apparatus according to this embodiment of the present invention, the system controller could provide, for example, the following information/recommendation, as shown in Table 2:

TABLE 2

| | System information provided at a decision distribution for two sensor principles as shown in Table 1. | | | | | | | | |
|---|---|---|---|---|---|---|---|---|---|
| CASE | 1 | 2 | 3 | 4 | 5 | 6 | 7 | 8 | 9 |
| INFO | DET POS | DET NEG | POS? REP | POS? REP | POS? SERV | NEG? SERV | POS? SERV | NEG? SERV | SERV NOW |

In Table 2, the message "DET POS" means that both sensor principles used are detecting bacterial growth. "DET NEG" indicates that both sensors are receiving clear signals, but the signals are typical for the absence of microorganisms. The message "POS? REP" shows that both sensors are receiving clear signals, that bacterial growth is likely, but a repeat experiment based on an alternative detection principle is recommended. In one instance, a proper alternate detection method is agar plating. The message "POS? SERV" indicates that one sensor could have a technical problem, but the other sensor is detecting bacterial growth. Depending on the structure of the automated blood culture instrument, it may be necessary to obtain technical service. Accordingly, "NEG? SERV" indicates that one sensor could have a technical problem, but the other sensor is receiving a clear signal indicating the absence of bacteria. Again, it may be necessary to obtain technical service. Finally, "SERV NOW" indicates that none of the sensors is receiving a clear signal, and that a technical problem is very likely.

Interpretation of the messages "POS? SERV" and "NEG? SERV" will depend on the structure of the particular blood culture instrument. It will also depend on the number of vials from which this message is obtained. If the individual sensors are independent, and if the message is obtained only for one vial, then a correct diagnosis will be difficult. If a group of sensors is interlinked by one or more con, on elements, and if the message is obtained for all vials of this group, then the interpretation is much easier.

FIGS. 3A to 3D show charts with plots of intensity versus time obtained using an apparatus according to the present invention, with data plots from a fluorescent carbon dioxide sensor (solid lines) and with detecting means based on scattered photon migration (dashed lines). The upper two charts represent tests for $N.$ $meningitidis$ 291 in an aerobic medium and the lower two charts represent tests for $N.$ $gonorrhoeae$ 115 in an aerobic medium. For each chart, both detecting means indicate microorganism presence at approximately the same time. The scattered photon method indicates a rapid reduction of light intensity being received by photodetector 46 when microorganism growth is detected. At the same time, however, the intensity of light being produced by the fluorescent sensor increases as microorganism growth is detected using the fluorescent sensor. Thus, both detecting means appear to be working equally well. Nevertheless, substantially more information is provided as compared to a one-principle instrument.

FIGS. 4A to 4D show four charts with plots of intensity versus time obtained using an apparatus according to the present invention, with data plots from a fluorescent carbon dioxide sensor (solid lines) and detecting means based on scattered photon migration (dashed lines). The upper two charts represent tests for $A.$ $Iwoffi$ 750 in an Aerobic medium and the lower two charts represent tests for $A.$ $faecalis$ 8750 in an aerobic medium. These charts were selected to show that in principle a fluorescent carbon dioxide detector can fail. The SPM detecting approach works as illustrated in FIGS. 3A to 3D, and indicates the presence of microorganisms. The fluorescent sensor, however, does not return results which would indicate the presence of microorganisms. Unlike in FIGS. 3A to 3D, the intensity of light emitted from fluorescent sensor 36 does not show a substantial increase over time. This suggests that either the detecting means based on the fluorescent sensor has failed because of a technical problem or one of the limitations of this detecting means, as discussed above, is present.

FIGS. 5A to 5D show charts with plots of intensity versus time obtained using an apparatus according to the present invention. It includes data plots from a fluorescent carbon dioxide sensor (solid lines) and detecting means based on scattered photon migration (dashed lines). The upper left chart represents a test for $F.$ $nucleatum$ 10953. The upper right chart represents a test for $B.$ $vulgatus$ 8482. The bottom left chart represents a test for $B.$ $fragilis$ 25285. The bottom right chart represents a test for $S.$ $aureus$ 25923. Each of these tests took place in an anaerobic medium. The detecting means based on the fluorescent sensor works as illustrated in FIGS. 3A to 3D, and indicates the presence of microorganisms. The SPM detecting approach does not return results which would indicate the presence of microorganisms. Unlike in FIGS. 3A to 3D and 4A to 4D, the intensity of light measured does not show a substantial change over time. This suggests that either the detecting means based on SPM has failed because of a technical problem or one of the limitations of this detecting means, as discussed above, is present.

Thus, while the preferred embodiments of the present invention have been described so as to enable one skilled in the art to practice the apparatus and method of the present invention, it is to be understood that variations and modifications may be employed without departing from the concept and intent of the present invention as defined in the following claims. For example, it should be appreciated that the invention is not limited to the specific detection principles described, namely fluorescence and scattered photon migration, but may include others. Accordingly, the preceding description is intended to be exemplary and should not be used to limit the scope of the invention. The scope of the invention should be determined only by reference to the following claims.

We claim:

1. An apparatus for detecting microorganisms in fluid samples, comprising:
 a sealable container;
 a plurality of detecting means for detecting microorganisms in said sealable container, each of said plurality of detecting means using a different microorganism detection principle, wherein one of said different microorganism detection principles is scattered photon migration; and said plurality of detecting means connected to a system controller, said system controller receiving data representing microorganism growth produced by each of said plurality of detecting means and combining said data to arrive at a final system determination regarding the presence of microorganisms in said sealable container.

2. An apparatus as recited in claim 1, further comprising a peripheral modem, said system controller being connected to said peripheral modem with said peripheral modem initiating a measurement process to obtain information concerning microorganism presence from said system controller.

3. An apparatus as recited in claim 1, wherein said data is analyzed within said system controller with each analysis being performed separately for each of said detecting means and a partial system answer being generated for each of said detecting means, each said partial system answer being compared to arrive at said final system determination.

4. An apparatus as recited in claim 3, wherein said partial system answer is generated according to one of three possible outcomes, "detection positive" which indicates the presence of microorganisms, "detection negative" which indicates the absence of microorganisms, and "decision impossible" which indicates a problem with said detecting means.

5. An apparatus as recited in claim 3, whereby said system controller cross-correlates said data when said data from more than one of said detecting means includes a low signal-to-noise ratio, in order to average noise contributions to said data.

6. An apparatus as recited in claim 1, further comprising an incubator for receiving said at least one sealable container.

7. An apparatus as recited in claim 1, wherein one of said detecting means includes a fluorescent sensor, said fluorescent sensor being excited through a light emitting means and a spectral filter being arranged between said light emitting means and said fluorescent sensor to block unwanted long-wavelength radiation, said fluorescent sensor selectively emitting fluorescence light, the intensity of said fluorescence light varying as microorganisms grow.

8. An apparatus as recited in claim 7, wherein a portion of said fluorescence light passes through an optical fiber, an end of said optical fiber being mounted within an opaque plate in front of a photodetector.

9. An apparatus as recited in claim 8, wherein a spectral filter is disposed between said opaque plate and said system controller to prevent scattered excitation light from reaching said photodetector.

10. An apparatus as recited in claim 7, wherein said light emitting means comprises a green light emitting diode.

11. An apparatus as recited in claim 7, wherein said fluorescent sensor is a fluorescent carbon dioxide sensor.

12. An apparatus as recited in claim 7, wherein said fluorescent sensor is spread along a portion of an inner surface of said at least one sealable container away from said light emitting means.

13. An apparatus as recited in claim 1, wherein said detecting means is based on scattered photon includes light emitting means introducing light into said at least one sealable container, and light reemerging from said sealable container being detected by a photodetector.

14. An apparatus as recited in claim 13, wherein a portion of said reemerging light passes through an optical fiber, an end of said optical fiber being mounted within an opaque plate in front of said photodetector.

15. An apparatus as recited in claim 13, wherein said light emitting means comprises a red light emitting diode.

16. A method for detecting microorganisms comprising the steps of:
(A) introducing a specimen into a container;
(B) monitoring selectively said container for microorganism growth with a plurality of detecting means, each of said plurality of detecting means using a different microorganism detection principle based on more than one of physical, chemical, and metabolic parameters, wherein one of said different microorganism detection principles is scattered photon migration;
(C) receiving and evaluating data representing microorganism growth generated by said plurality of detecting means to arrive at a plurality of partial system answers, each of said plurality of partial system answers corresponding to one of said plurality of detecting means; and
(D) linking said plurality of partial systems answers to arrive at a final system determination regarding the presence of microorganisms in said container.

17. A method as recited in claim 16, further comprising the step of cross-correlating said data when said data from more than one of said detecting means includes a low signal-to-noise ratio, in order to average noise contributions to said data.

18. A method as recited in claim 16, further comprising the step of limiting said plurality of partial system answers to one of three possible outcomes, "detection positive" which indicates the presence of microorganisms, "detection negative" which indicates the absence of microorganisms, and "decision impossible" which indicates a problem with said plurality of detecting means.

19. An apparatus for detecting microorganisms, comprising:
a sealable container maintained at a temperature above ambient to promote optimum growth of microorganisms therein;
a plurality of detecting means for detecting microorganism growth in said sealable container, each of said plurality of detecting means using a different microorganism detection principle, wherein one of said different microorganism detection principles is scattered photon migration and at least one of said detecting means is located within said sealable container and the others are located outside of said sealable container; and
each of said plurality of detecting means being connected to a system controller, said system controller selectively activating each of said plurality of detecting means, receiving data representing microorganism growth from each of said plurality of detecting means, and generating a plurality of partial system answers based upon said data received from each of said plurality of detecting means, each of said plurality of partial system answers corresponding to one of said plurality of detecting means and having one of three possible outcomes, "detection positive" which indicates the presence of microorganisms, "detection negative" which indicates the absence of microorganisms, and "decision impossible" which indicates a problem with said detecting means with each of said partial system answers being compared to arrive at a final system determination of the presence of microorganisms in said sealable container.

20. An apparatus as recited in claim 19, wherein a first detecting means includes a fluorescent sensor which is excited through a green light emitting diode, a spectral filter being arranged between said green light emitting diode and said fluorescent sensor to block unwanted long-wavelength radiation, said fluorescent sensor being spread along a portion of an inner surface of said sealable container away from said green light emitting diode and selectively emitting fluorescence light, the intensity of said fluorescence light varying as microorganisms grow, said intensity being detected by a photodetector, a portion of said fluorescence light passing through an optical fiber of said first detecting means, an end of said optical fiber being mounted within an opaque plate in front of said photodetector and a special filter being disposed between said opaque plate and said photodetector to prevent back-scattered green excitation light from reaching said photodetector.

21. An apparatus as recited in claim 20, wherein said detecting means based on scattered photon migration includes a red light emitting diode adjacent to said sealable container, said red light emitting diode passing light through said sealable container, a portion of said light passing through an optical fiber distinct from said optical fiber of said first detecting means, an end of said distinct optical fiber being mounted within said opaque plate in front of said photodetector.

* * * * *